United States Patent [19]
Weintraub et al.

[11] Patent Number: 5,486,511
[45] Date of Patent: Jan. 23, 1996

[54] 4-AMINO-17β-(CYCLOPROPYLOXY)ANDROST-4-EN-3-ONE, 4-AMINO-17β-(CYCLOPROPYLAMINO)ANDROST-4-EN-3-ONE AND RELATED COMPOUNDS AS $C_{17-20}$ LYASE AND 5α-REDUCTASE

[75] Inventors: Philip M. Weintraub, Cincinnati; Cynthia A. Gates, Fairfield; Michael R. Angelastro; Timothy T. Curran, both of Cincinnati; J. O'Neal Johnston, Milford, all of Ohio

[73] Assignee: Merrell Dow Pharmaceuticals Inc., Cincinnati, Ohio

[21] Appl. No.: 231,434

[22] Filed: May 2, 1994

Related U.S. Application Data

[63] Continuation-in-part of Ser. No. 209,501, Mar. 16, 1994, abandoned, which is a continuation-in-part of Ser. No. 66,744, May 25, 1993, abandoned.

[51] Int. Cl.⁶ .......................... A61K 31/565; C07J 1/00
[52] U.S. Cl. .......................... 514/178; 514/177; 514/180; 514/181; 552/515
[58] Field of Search ................. 552/515; 514/178, 514/181, 177, 180

[56] References Cited

U.S. PATENT DOCUMENTS

| | | |
|---|---|---|
| 3,637,668 | 1/1972 | Laurent et al. . |
| 3,732,209 | 5/1973 | Fahrenboltz et al. . |
| 4,891,367 | 1/1990 | Angelastro et al. . |
| 4,966,897 | 10/1990 | Antelastro et al. . |
| 5,120,840 | 6/1992 | Weintraub et al. .......... 552/515 |
| 5,130,424 | 7/1992 | Weintraub .......... 552/515 |
| 5,143,909 | 9/1992 | Weintraub et al. . |
| 5,189,032 | 2/1993 | Weintraub .......... 552/515 |
| 5,218,110 | 6/1993 | Weintraub . |
| 5,218,810 | 6/1993 | Weintraub .......... 552/515 |
| 5,318,961 | 6/1994 | Weintraub et al. .......... 514/177 |

FOREIGN PATENT DOCUMENTS

| | | |
|---|---|---|
| 0286578 | 10/1988 | European Pat. Off. . |
| 0291290 | 11/1988 | European Pat. Off. . |
| 204888 | 12/1980 | United Kingdom . |
| 2171100 | 8/1986 | United Kingdom . |

OTHER PUBLICATIONS

Biochemistry; J. David Rawn; Chapter 19.6; pp. 564–569; *Steroid Hormones Are Derived from Cholesterol.* (1989).
Henderson's Dictionary of Biological Terms; 10th Ed.; Eleanor Lawrence; p. 253. (1989).
The Journal of Urology; vol. 131, *Biological Effects of Hormonal Treatment Regimens on a Transplantable Human Prostatic Tumor Line (PC–82)*; Van Steenbrugge, et al.; pp. 812–817 (1984).
Cancer Research 52, 2538–2544; *Sustained Release Formulations of Luteinizing Hormone–releasing Hormone Antagonist SB–75 Inhibit Proliferation and Enhance Apoptotic Cell Death of Human Prostate Carcinoma (PC–82) in Male Nude Mice*[1]; Redding, et al. (1992).
Journal of Clinical Endocrinology and Metabolism; vol. 57, No. 4; *Site of Action of Low Dose Ketoconazole and Androgen Biosynthesis in Men\**; Santen, et al; pp. 732–736 (1983).
Cancer Supplement; vol. 71, No. 3; *Ketoconazole and Liarozole in the Treatmen tof Advance Prostatic Cancer*, Mahler, et al,; pp. 1068–1073 (1993).
Arch Intern Med; vol. 142, Nov. 1982, *Ketoconazole Blocks Testosterone Synthesis;* Pont et al; pp. 2137–2140 (1982).
The Journal of Urology, vol. 132; *Ketoconazole Therapy in Advance Prostatic Cancer*, Trachtenberg; pp. 61–63 (1984).
The Journal of Urology, vol. 137; *Long–Term Experience with High Dose Ketoconazole Therapy in Patients with Stage D2 Prostatic Carcinoma*, Pont; pp. 902–904 (1987).
Chem Abst., 17971f, vol. 64(1666), (1966).
Derwent Abstract 9186 (JP 17673/673) (1963).
M. Davis et al., *J. Chem. Soc.* (C) 1688–97 (1966).
A. Ercoli et al., *Chem & Indus.*, 1284–85 (Jul. 14, 1962).
G. Falconi, *Hormonal Steroids, Proc. Int'l Congr. Hormonal Steroids*, 2:143–53 (1965).
R. Gardi et al., *Steroids* 19:639–47 (1972).
Goodman & Gilman, 7th Ed., 1448–49 (1980).

*Primary Examiner*—Kimberly J. Kestler
*Attorney, Agent, or Firm*—Craig G. Svoboda

[57] ABSTRACT

This invention is directed to 4-amino-17β-(cyclopropyloxy)androst-4-en-3-one, 4-amino-17β-(cyclopropylylamino)androst-4-en-3-one and related compounds, a process for their synthesis, a pharmaceutical composition having $C_{17-20}$ lyase and 5α-reductase inhibitory activity, the use of the present compounds as $C_{17-20}$ lyase and 5α-reductase inhibitors and also to a method for using such compounds in the treatment of androgen and/or estrogen dependent disorders, including bengin prostatic hyperplasia, breast cancer and prostatic cancer. The 4-amino compounds are prepared by the reaction of the appropriate 4,5-epoxide with sodium azide in an inert solvent in the presence of a catalytic amount of strong acid under appropriate reaction conditions. Alternatively, the 4-amino compounds are prepared by first nitration and then reduction of the appropriate steroid under appropriate reaction conditions.

38 Claims, No Drawings

4-AMINO-17β-(CYCLOPROPYLOXY)ANDROST-4-EN-3-ONE, 4-AMINO-17β-(CYCLOPROPYLAMINO)ANDROST-4-EN-3-ONE AND RELATED COMPOUNDS AS $C_{17-20}$ LYASE AND 5α-REDUCTASE

The present application is a continuation-in-part of application Ser. No. 08/209,501, filed Mar. 16, 1994, and now abandoned which is a continuation-in-part of application Ser. No. 08/066,744, filed May 25, 1993, now abandoned.

BACKGROUND OF THE INVENTION

The enzyme steroid $C_{17,20}$ lyase cleaves the 17–20 carbon-carbon bond in steroids having a two carbon side chain at the 17β-carbon position to form important precursor molecules to the formation of testosterone, 5α-dihydrotestosterone and the estrogens, principally estrone and estradiol. Compounds which inhibit this enzyme would thus serve to inhibit the formation of the indicated precursors and thereby be useful in the treatment of various androgenic as well as estrogenic disorders. A treatment incorporating such enzymatic inhibitors is not limited to the origin of the precursor molecule, such as various organ ablation techniques which are currently known. For example, while orchiectomy will effectively reduce gonadal androgen, it will have not have significant effect upon adrenal androgen production. Moreover, such an enzymatic treatment is a much more focused treatment in that it is directed to the immediate hormonal imbalance believed responsible for the condition, as opposed to a broad spectrum remedy which not only affects the particular symptom, but causes permanent endocrine defects necessitating life-long dependency on replacement therapy.

It is further known that certain types of breast cancers are estrogen dependent. Adrenalectomy, ovariectomy and hypophysectomy have been employed as well as nonsurgicial techniques resulting in tumor regressions. It has been shown that human patients with advanced breast cancer, who are administered estrogen biosynthesis enzyme inhibitors, show dramatically reduced plasma estradiol levels and improved therapeutic effects, at least as effective as adrenalectomy. (Jean Van Wauve and Paul A. J. Janssen, *Journal of Medicinal Chemistry*, 32, 10:2231–2239).

Prostatic cancer, or neoplastic tissue disorders which originate in the parenchymal epithelium of the prostate is one of the most common malignancies among men, and exhibits one of the highest cancer-specific deaths of all malignant carcinomas. It is known that patients with metastatic prostate cancer respond positively to hormonal therapy. It is reported by Cookson and Sarosdy that androgen ablation has had a positive, beneficial response for as high as 60% to 80% for all patients tested. (Cookson C. S. and Sarosdy, M. F., South Med. J 87:1–6).

More specifically, $C_{17,20}$ lyase inhibitors would be useful in the treatment of hormonal dependent prostatic carcinoma, prostatic hyperplasia, virilism, congential adrenal hyperplasia due to 21-hydroxylase deficiency, hirsutism, hormonal dependent breast cancer, polycystic ovarian syndrome correlated with elevated $C_{17,20}$ lyase activity as well as other neoplastic tissue disorders such as endometrial, hepatocellular and adrenal carcinomas.

The enzyme steroid 5α-reductase, present in mammalian tissues including skin, male genitalia and the prostate, catalyzes the conversion of testosterone (17β-hydroxy-androstan-4-en-3-one) into dihydrotestosterone or DHT (17β-hydroxy-5α-androst-3-one), which is also known as stanolone. DHT is a more potent androgen than testosterone, and acts as an end-organ effecter in certain tissues, particularly in mediating growth. DHT formation can occur in certain tissues themselves by the action of 5α-reductase. In the treatment of androgen dependent disorders, such as benign prostatic hyperplasia and prostatic cancer, including hormonal dependent carcinoma, the inhibition of DHT would be highly desirable.

The conversion of testosterone to DHT itself can be associated with various androgenic disorders, especially when DHT levels build up to excessive amounts. For example, high levels of DHT in the skin has been associated in the pathogenesis of acne, including acne vulgaris.

Agents which have the ability to inhibit both $C_{17-20}$ lyase and 5α-reductase would not only inhibit DHT production, but also testosterone formation. In inhibiting the principal androgenic steroidal hormones, such compounds would have enhanced utility in the treatment of androgen disorders.

SUMMARY OF THE INVENTION

The present invention is directed to 4-amino-17-(cyclopropylxy)androst-4-en-3-one, 4-amino-17-(cyclopropylamino)androst-4-en-3-oneand related compounds and to the use of these compounds in the treatment of conditions which would be affected by inhibition of $C_{17-20}$ lyase and/or 5α-reductase, including androgen and estrogen mediated disorders, such as, for example benign prostatic hyperplasia, estrogen dependent breast cancer and androgen mediated prostatic cancer. More particularly, the present invention is directed to a group of compounds, and their pharmaceutically acceptable salts, having the following general formula:

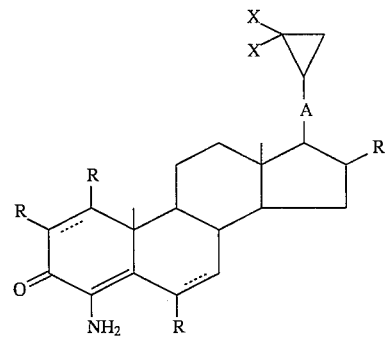

wherein A is O or NH and each R is independently selected from the group consisting of hydrogen and $C_1$-$C_4$ lower alkyl; each X is independently selected from the group consisting of hydrogen, halogen, and methyl; and the dotted lines indicate the optional presence of a double bond. Preferred compounds are those in which R and X are hydrogens.

DETAILED DESCRIPTION OF THE INVENTION

As used herein, the term "$C_{1-4}$ lower alkyl" means a straight or branched chain hydrocarbon radical from one to four carbon atoms. For example, methyl, ethyl, propyl, isopropyl, n-butyl, s-butyl, t-butyl and the like.

As used herein, the term "pharmaceutically acceptable salts" is readily determinable by one of ordinary skill in the art and means an acid addition salt which does not pose a significant toxic effect to the patient and which possesses desireable pharmaceutical handling and formulation properties. Such salts can be either inorganic or organic and may be hydrated or substantially anhydrous. Illustrative inorganic acids which form suitable salts include hydrochloric, hydrobromic, sulphuric, phosphoric acid and metal salts such as sodium monohydrogen orthophosphate and potassium hydrogen sulfate. Illustrative organic acids which form suitable salts include the mono, di and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, and sulfonic acids such as methane sulfonic acid and 2-hydroxyethane sulfonic acid.

The compounds of the present invention are obtained by starting with the appropriate 4,5-epoxy compound of the formula:

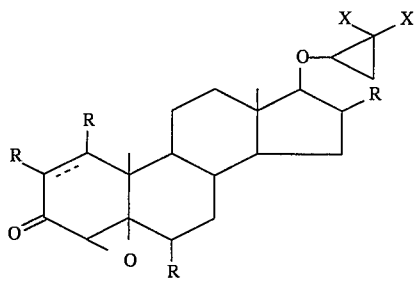

wherein R, X and the dotted lines are defined as above. To obtain the compounds of the present invention which do not have a double bond at the 6-position, the indicated 4,5-epoxy compound is reacted with sodium azide in an inert solvent, such as dimethyl sulfoxide in the presence of a catalytic amount of sulfuric acid. The reaction mixture is heated at about 60° C. to give the corresponding 4-azido-4-ene. This azido compound is then heated with triphenylphosphine in an aqueous inert solvent to give the desired amino compound. Aqueous tetrahydrofuran is an example of a useful solvent for the reaction.

To obtain the 4-amino-4,6-diene compounds of the present invention, the epoxy compound referred to above is reacted with sodium azide in an inert solvent such as dimethyl sulfoxide. The reaction is carried out in the presence of a catalytic amount of a strong acid, such as sulfuric acid, with heating at 100° C. No effort is made to isolate any intermediates but it appears that the epoxide is first opened to give the 4-azido-4-ene. Under the reaction conditions used, tile azido compound loses nitrogen, a putative azirine forms, and this opens to give the desired 4-amino-4,6-diene.

The 4,5-epoxy compounds, used as the starting material above, are obtained by the base catalyzed epoxidation of the appropriate corresponding 4-ene using 30% aqueous hydrogen peroxide. For those compounds containing a double bond at the 1-position, it is more convenient to introduce that unsaturation after the epoxide is formed. Thus, for example, treatment of a 4,5-epoxy 3-ketone with dichlorodicyanoquinone gives the corresponding $\Delta^1$ epoxide compound. The epoxide products obtained above are generally mixtures of the α- and β-epoxides with the β-epoxide being the preponderant product. In any case, further reaction of the epoxides with sodium azide, according to the procedures described earlier, gives the desired 4-amino products.

Alternatively, the compounds of the present invention may be obtained by reducing the appropriate 4-nitro,4-ene steroid compound to get the desired 4-amino steroid. The 4-nitro-4-ene compound may be obtained by reacting the appropriate steroid under suitable conditions with a strong base under conditions sufficient to create the thermodynamic dienolate, which can then be nitrated by any suitable nitrating agent, for example, isopropyl nitrate. The resulting 4-nitro compound may then be reduced by any known means, for example, chemically or catalytically to give the desired 4-amino-4-ene steroid.

The present compounds are useful as inhibitors of steroid $C_{17-20}$ lyase and 5α-reductase and thus inhibit the formation of androgenic steroids, including testosterone. Consequently, they are useful for treating various androgen-dependent disorders. As $C_{17-20}$ lyase inhibitors, they are also useful for the treatment of various estrogen-dependent disorders. The present invention thus also encompasses a method for treating androgen and/or estrogen dependent disorders which comprises administering to a patient suffering from such a disorder an effective enzyme inhibitory amount of a compound of the present invention. As used herein, patient is taken to mean warm blooded mammals, including humans, primates, dogs, cattle, cats, horses, sheep, mice, rats and pigs.

More particularly, as androgenic inhibitors the present compounds are useful in the treatment of prostatic cancer including androgen dependent prostatic carcinoma, virilism, androgenic alopecia, seborrhea and female hirsutism. Because the present compounds are also 5α-reductase inhibitors, they have particular utility as treatment of dihydrotestosterone (DHT) mediated diseases, such as benign prostatic hyperplasia, androgen alopecia, seborrhea, female hirsutism, polycystic ovarian syndrome and acne disorders, including acne vulgaris.

Because of their ability to inhibit steroid $C_{17,20}$ lyase, a component of the estrogen biosynthetic pathway, the present compounds can inhibit estrogen biosynthesis. As a result, the present compounds have utility as antifertility agents to prevent ovulation or implantation in females, as well as to reduce mating behavior in males, where aromatization is a necessary event for such behavior. Since the present compounds can lower circulating estrogen levels, they can effectively prevent the biologically active estrogens from reaching endocrine tumors. In addition, since the present compounds can reduce estrogen biosynthesis in tumors capable of endogenous estrogen synthesis, the present compounds are capable of inducing remissions in breast cancer, including metastatic tumors. Furthermore, the present compounds have utility in the treatment of ovarian, uterine and pancreatic tumors as well as disease conditions such as galactorrhea, McCume-Albright syndrome, benign breast disease, and endometriosis. As $C_{17,20}$ lyase inhibitors, the compounds are further useful to treat other neoplastic tissue disorders such as endometrial, hepatocellular and adrenal carcinoma.

The activity of the present compounds as inhibitors of steroid $C_{17,20}$ lyase was established using microsomal preparations of the steroid $C_{17,20}$ lyase enzyme from human or laboratory animal testes. Human testes used for this purpose were obtained from therapeutic orchiectomies. Specifically, microsomes were isolated from human, cynomolgus monkey, dog, rat or athymic nude mouse testicular tissue. The compound to be tested was dissolved in dimethyl sulfoxide and diluted in 0.05M potassium phosphate buffer to give the desired concentrations of the test compound. The potassium phosphate buffer was at pH 7.4 for the human, monkey and dog lyase assays and at pH 7.2 for the rat and athymic nude mouse lyase assays. Assays also contained 1 mM NADPH, 5 mM glucose-6-phosphate, 1 IU/ml glucose-6-phosphate dehydrogenase (an NADPH regenerating system) and microsomal protein in a total volume of 0.2 mL. Control assays contained all components including dimethyl sulfoxide, but with no test compound. All assays were performed in duplicate. For determination of time dependent $C_{17,20}$ lyase inactivation, the test compound was incubated with 20 to 60 µg/ml microsomal protein, buffer, and the NADPH regenerating system described above at 34° C. for 0 or 40 minutes. Aliquots (180 µl) were then removed and assayed for enzyme activity by addition to tritiated steroid substrate plus unlabeled steroid substrate to give a 200 µl total assay volume, and were subsequently incubated at 34° C. for 6 minutes. For determination of reversible inhibition by the test compound, the reaction was initiated by addition of substrate. The radiolabeled substrate used for human, cynomolgus monkey and dog lyase was [7-$^3$H]-17α-hydroxypregnenolone, 11.2 Ci/mmole, 0.2 µCi total activity per assay. Unlabeled 17α-hydroxypregnenolone was added to give a total concentration of 1.0 µM or 0.3 µM for the human and monkey enzymes, and 0.08 µM for the canine enzyme. The values for the $K_m$ of 17α-hydroxypregnenolone for human, monkey and dog lyase are 0.30 µM, 0.11 µM and 0.06 µM, respectively. The radiolabeled substrate used for the rodent enzymes were [1,2-$^3$H]-17α-hydroxyprogesterone (40–57 Ci/mmol; 0.2 µCi per assay). Unlabeled 17α-hydroxyprogesterone was added to give a total concentration of 0.1 µM for the rat enzyme ($K_m$=0.1 µM) and 0.03 µM ($K_m$=0.03 µM) for the athymic nude mouse enzyme. The total assay volume was 200 µl. The complete assay was incubated at 34° C. for 6 minutes. Each reaction was stopped by the addition of 5 ml of chloroform:methanol (2:1). Carrier steroids representing substrate and products and 0.8 ml of water were also added at this time. The carrier steroids for the human, monkey and dog lyase assays were 17α-hydroxypregnenolone, dehydroepiandrosterone and androstenediol. Carrier steroids for the rodent lyase assays were 17α-hydroxyprogesterone, androstenedione, and testosterone. The steroids were extracted by the method of Moore and Wilson (Methods in Enzymol., eds. O'Malley, B. W. and Hardman, J. G. 36, 1975, p. 466–474), the organic phase containing the steroids was evaporated using nitrogen gas, the residues dissolved in 18% tetrahydrofuran (v/v) in hexane, and the steroids were separated by HPLC on a Si60 (5 um) column (250×4 mm) using a gradient of 18–22% tetrahydrofuran (v/v) in hexane. Radioactivity in the steroid peaks was measured by a Radiomatic Model HS Flo-One detector.

The enzyme activity for each incubate was calculated from the percent conversion of substrate to products, and the results were expressed as percent inhibition of control. IC$_{50}$ values were determined by fitting these data to the two parameter equation in an appropriate computer program. The $K_i$ and $k_{inact}$ for time dependent inhibitors were determined by graphical analysis of Kitz-Wilson plots. When the compounds of the present invention were tested in the above procedure using human lyase, the following results were observed:

TABLE 1

Enzymatic inhibition of human, canine, rat and nude mouse lyase

| Compound | Enzyme | Conc. (µM) | Preincubation time (min.) | % Inhibition |
| --- | --- | --- | --- | --- |
| 1 | Human | 10 | 40 | 98 |
|   |       | 10 | 0  | 95 |
|   |       | 1  | 40 | 84 |

TABLE 1-continued

Enzymatic inhibition of human, canine, rat and nude mouse lyase

| Compound | Enzyme | Conc. (µM) | Preincubation time (min.) | % Inhibition |
| --- | --- | --- | --- | --- |
|   |       | 1    | 0  | 69 |
| 2 | Human | 10   | 40 | 99 |
|   |       | 10   | 0  | 96 |
|   |       | 1    | 40 | 86 |
|   |       | 1    | 0  | 79 |
|   | Canine | 1   | 40 | 57 |
|   | Rat    | 0.1 | 40 | 70 |
|   | Nude mouse | 0.01 | 40 | 84 |

KEY:
1 4-amino-17β-(cyclopropyloxy)-androsta-4,6-dien-3-one
2 4-amino-17β-(cyclopropyloxy)-androst-4-en-3-one Using cynomolgus monkey $C_{17,20}$ lyase, 4-amino-17β-cyclopropyloxyandrost-4-en-3-one showed a $K_i$ of 286 nM and a $k_{inact}$ of 0.0007 sec$^{-1}$. Similarly, 4-amino-17β-cyclopropyloxyandrosta-4,6-dien-3-one yielded a $K_i$ of 339 nM and a $k_{inact}$ of 0.0009 sec$^{-1}$.

The activity of the present compounds as inhibitors of steroid 5α-reductase was determined using microsomal preparations of the 5α-reductase enzyme from laboratory prostate tissue. Specifically, microsomes were isolated from cynomolgus monkey prostate tissue. Protein concentration of the microsomal preparations was determined prior to use of the samples. Individual assays of cynomolgus monkey prostatic 5α-reductase activity contained 0.1M potassium phosphate-sodium citrate buffer (K-Na buffer, 1:1), pH 5.6, 0.1% bovine serum albumin (w/v), 1.0 mM sodium EDTA, 7 to 96 µg of microsomal protein, 1.0 mM NADPH, 5.0 mM glucose-6-phosphate, 1 IU/mL glucose-6-phosphate dehydrogenase, [1,2-$^3$H]-testosterone (0.15 µCi), unlabeled testosterone to yield the desired concentration of substrate, and inhibitor which was dissolved in dimethyl sulfoxide (DMSO) then diluted in K-Na buffer to yield a final assay concentration of 0.1% (v/v) DMSO. The same buffer and DMSO without inhibitor were used in control assays. Background radioactivity was determined from assays containing all components except enzyme. Assays were performed in duplicate. The reaction was initiated by the addition of testosterone and incubated for 20 minutes at 25° C. in a Dubnoff® shaker incubator. Compound to be tested for inhibition was added simultaneously with testosterone. The total volume of the assay was 100 µL.

The 5α-reductase reactions were terminated by the addition of 5 mL chloroform-methanol (2:1) and 0.9 mL water. The carrier steroids were added in the form of 2.5 µg each of testosterone, dihydrotestosterone, and 3,17-androstanediol. The steroid metabolites were then extracted according to the procedure of Moore and Wilson (Methods in Enzymology, O'Malley, B. W. and Hardman, J. G. eds., 36, 1975, pp. 466–474. The organic phase containing the steroids was evaporated using nitrogen gas, the residues were dissolved in 3% (v/v) isopropanol in hexane. The steroids were then separated by normal phase HPLC on a LiCrosorb® DIOL derivative silica gel column (10 µm; 4×250 mm) with a 3% to 7.5% isopropanol in hexane gradient, followed by isocratic conditions of 75% (v/v) isopropanol in hexane. Radioactivity in the steroid peaks was measured using a Packard® Radiomatic model HS Flo-One® detector. IC$_{50}$ values were obtained using six concentrations of inhibitor, while $K_i$ values were determined from four concentrations of inhibitor. The data from these experiments were fitted to an appropriate two parameter computer model to determine the actual IC$_{50}$ and $K_i$ value.

The assay was linear with time to 30 minutes under these conditions. For $IC_{50}$ determinations, a single concentration of testosterone at the $K_m$ level was used. Testosterone concentration was varied over a range of 0.5 $K_m$ to 8 $K_m$ for determination of inhibition mechanism and $K_i$ values. The $K_m$ values of testosterone, determined in multiple experiments, ranged form 0.025 µM–0.091 µM for cynomolgus 5α-reductase.

Using the above procedure on cynomolgus monkey 5α-reductase, 4-amino-17β-cyclopropyloxyandrost-4-en-3-one gave an $IC_{50}$ of 7.4 nM and a $K_i$ of 7.8±0.7 nm. Similarly, 4-amino-17β-cyclopropyloxyandrosta-4,6-dien-3-one yielded an $IC_{50}$ of 2.8 nM.

The utility of the present compounds as therapeutic agents for the treatment of prostrate cancer was demonstrated by the in vivo tumor model described in Hoehn W. et al., *Prostrate* 1:95–104 (1980); Van Steenbrugge, J. J., et al., *Urology* 131:812–817 (1984). In this model, human prostatic tumor xenographs (PC-82) are grown in athymic mice. The tumors are serially transplantable, androgen-responsive, slow-growing (i.e. 20–30 days for tumor volume to double) and are moderately differentiated human prostatic adenocarcinoma. These tumors will regress following androgen ablation with a half-life of 18 days (van Weerden, W. M. et al., Prostate 23:149–164 (1993).

The above tumor model of androgen-dependent human prostatic cancer was utilized to evaluate 4-amino-17β -(cyclopropyloxy)androst-4-en-3-one for inhibition of prostatic tumor growth following daily oral treatment at 30 and 100 mg/kg/day (See Table 2). Two control groups were tested, including one which received only the delivery vehicle and another which were bilaterally castrated. Tumor volumes were measured three times per week using a digital caliper using the formula: V $(mm^3)=d_1 \times (d_2)^2/2$ were $d_1$ is the length and $d_2$ the width. The relative percent change in tumor volume is based on the mean tumor volume of the vehicle control groups at week 0 being set equal to 100%.

TABLE 2

Inhibition of Human Prostatic Tumor Growth
-Tumor volume $(mm^3)$
-Relative percent tumor volume compared to vehicle control at beginning of timed period

| Treatment | Time (weeks) | | |
|---|---|---|---|
| | 0 weeks | +2 weeks | +4 weeks |
| Vehicle alone | 515 ± 122 | 828 ± 166 | 1919 ± 616 |
| | 100% | 161% | 373% |
| 30 mg/kg/day | 541 ± 71 | 771 ± 108 | 1305 ± 309 |
| | 105% | 150% | 253% |
| 100 mg/kg/day | 426 ± 49 | 601 ± 66 | 840 ± 86 |
| | 83% | 117% | 163% |
| Castrated | 456 ± 44 | 310 ± 48 | 227 ± 65 |
| | 89% | 60% | 44% |

In Table 2, the castrated group of control mice establish the androgen-dependency of the PC-82 prostate tumors, while the data establishes prolonged inhibition of human prostatic tumor growth following daily oral treatment with 4-amino-17β-(cyclopropyloxy)androst-4-en-3-one. As a result, it is shown that 4-amino-17β-(cyclopropyloxy)androst- 4-en-3-one induces a decrease in androgenic dependent growth of human prostatic tumors.

In the treatment of the various androgen and estrogen dependent disorders described earlier, the compounds of the present invention may be administered orally to the patient being treated to achieve the particular effect desired. The compounds of the present invention can also be administered in the form of a pharmaceutical preparation, and may further by incorporated into sustained delivery devices. As used herein, the term "effective inhibitory amount", is such amount wherein an enzyme inhibitory effect is achieved sufficient to cause a therapeutic effect in the patient. The exact amount of compound to be administered will vary over a wide range, depending principally upon patient type and size. For example, depending on the patient to be treated, and the severity of the condition being treated, the effective inhibitory amount of compound administered can vary from about 0.625 to 200 mg/kg of body weight per day and is preferably from about 0.5 to 100 mg/kg of body weight per day. Unit dosages for oral administration may contain, for example, from 10 to 500 mg of a compound of the invention. Alternatively, the present compounds can be administered parenterally, for example, intravenously, intraperitoneally, intramuscularly, subcutaneously, including release from implants as well as the injection of the active ingredient and/or composition directly into the tissue or tumor sites.

In practicing the method of this invention, the active ingredient is preferably incorporated in a composition containing a pharmaceutical carrier and from about 5 to about 90% by weight of the cyclopropyl steroid. The term "pharmaceutical carrier" refers to known pharmaceuticals excipients useful in formulating pharmaceutically active compounds for internal administration to animals, and which are substantially nontoxic and nonsensitizing under conditions of use. The compositions can be prepared by known techniques for the preparation of suitable delivery vehicles which may contain suitable excipients known to be useful in the preparation of the particular type of composition desired. For example, tablets, lozenges, capsules, powders, aerosol sprays, aqueous or oily suspensions, syrups, elixirs and solution for injection may be suitable delivery vehicles. Suitable pharmaceutical carriers and formulation techniques are found in standard texts, such as *Remington's Pharmaceutical Sciences*, Mack Publishing Company, Easton, Pa., which is herein incorporated by reference.

For oral administration, the compounds can be formulated into solid or liquid preparations, such as capsules, pills, tablets, troches, powders, solutions, suspensions, or emulsions. The solid unit dosage forms can be a capsule which can be of the ordinary gelatin types containing the active compound and a carrier, for example, lubricants, and inert filler such as lactose, sucrose and corn starch. In another embodiment, an active compound of the invention can be tableted with conventional tablet bases such as lactose, sucrose and corn starch in combination with binders such as gum acacia, corn starch, alginci acids and a lubricant such as stearic acid or magnesium stearate.

For parental administration, the compounds may be administered as injectable dosages of a solution or suspension of the compound in a physiological acceptable diluent with a pharmaceutical carrier which can be a sterile liquid such as water-in-oil with or without the addition of a surfactant and other pharmaceutically acceptable excipients. Illustrative of oils which can be employed in the preparations are those of petroleum, animal, vegetable or synthetic origin. For example, there may be mentioned peanut oil, soybean oil, and mineral oil. In general, water, saline, aqueous dextrose and related sugar solutions, ethanols and glycols, such as propylene or polyethylene glycol are preferred liquid carriers, particularly for injectable solutions.

The compound can be administered in the form of a cutaneous patch, a depot injection, or implant preparation which can be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers and synthetic silicones, for example, Silastic® silicone rubber manufactured by Dow Corning Corp. Further information on suitable pharmaceutical carriers and formulation techniques are found in standard texts such as *Remington's Pharmaceutical Sciences*.

The following examples are presented to illustrate the preparation of compounds within the present invention but they should not be construed as limiting the invention in any way.

EXAMPLE 1

4-Azido-17β-(cyclopropyloxy)androst-4-en-3-one

To a solution of 17β-(cyclopropyloxy)androst-4-en-3-one (10.9 g, 33.44 mM) in methanol (80 ml) and dichloromethane (60 ml) cooled to 15° C. in a water bath was added 30% hydrogen peroxide (8.2 ml) and then a solution of sodium hydroxide (0.58 g) in water (3.8 ml). After 4 hours at room temperature, most of the solvent was removed and the residue was diluted with water (300 ml) and extracted with dichloromethane (1L). The organic layer was separated, dried over magnesium sulfate, filtered and concentrated to a liquid which was purified by flash chromatography ($SiO_2$, toluene—5% ethyl acetate) to give a mixture of α and β-epoxides (5.6 g, 48.7%). IR 1724 $cm^{-1}$; MS (CI) m/z 345 (100%, $M^+$+1); $^1$H NMR ($CDCl_3$) 0.38–0.60 (4H, m, 2×cyclopropyl $CH_2$), 0.77 (major)+0.78 (3H, pr s, $C_{18}$-Me's), 1.15 (s, $C_{19}$-Me), 2.97 (major)+3.04 (1H, pr s, $C_4$-H's), 3.25–3.33 (1H, m, OCH), 3.45 (1H, dd, $C_{17\alpha}$-H).

To a vigorously stirred mixture of the above epoxide (3.6 g, 10.4 mM) in dimethylsulfoxide (DMSO) (80 ml) was added sodium azide (11 g, 169 mM) and then concentrated sulfuric acid (0.74 ml). After stirring at 60° C. for 90 minutes, the reaction mixture was cooled to room temperature and poured into cold water. The solids were collected by filtration, washed with water and dried to give a yellow solid. The crude product was purified by flash chromatography ($SiO_2$, toluene—20% hexane) to give 4-azido-17β-(cyclopropyloxy)androst-4-en-3-one (1.56 g, 42.7%) mp 103.5°–105.5° C. (aq $Me_2CO$). IR 2116, 1674, 1592 $cm^{-1}$; MS (CI) m/z 370 (3%, $M^+$+1), 342 (50%, $M^+$+1-$N_2$), 284 (100%, $M^+$+1-$N_2$-$C_3H_6O$); $^1$H-NMR ($CDCl_3$) 0.38–0.60 (4H, m- 2×cyclopropyl ($CH_2$'s), 0.79 (3H, s, $C_{18}$-Me), 1.18 (s, $C_{19}$-Me), 3.02 (1H, dq, $C_6$-H), 3.25–3.33 (1H, m, OCH), 3.43 (1H, t, $C_{17\alpha}$-H); $^{13}$C NMR ($CDCl_3$) 88.83, 128.46, 155.09, 193.22.

EXAMPLE 2

4-Amino-17β-(cyclopropyloxy)androst-4-en-3-one

A stirred solution of 4-azido-17β-(cyclopropyloxy)androst- 4-en-3-one (1.32 q, 3.57 mM), triphenylphosphine (1.14 g, 4.97 mM), tetrahydrofuran (25 ml) and water (8 ml) was heated to reflux for 15 hours. The reaction was cooled and most of the solvent was evaporated. The residue was dissolved in dichloromethane, loaded onto a column of $SiO_2$ and flash chromatographed (toluene—10% ethyl acetate) to give 4-amino-17β-(cyclopropyloxy)androst-4-en-3-one (0.53 g 43.1%), mp 85°–88° C. IR 3446, 3363, 1672, 1584 $cm^{-1}$; MS (CI) m/z 344 (100%, $M^+$+1), $^1$H NMR ($CDCl_3$), 0.38–0.61 (4H, m, 2× cyclopropyl ($CH_2$'s), 0.74 (s, $C_{18}$-Me), 1.15 (s, $C_{19}$-Me), 3.25–3.33 (m, OCH), 3.44 (t+br s, $C_{17}\alpha$-H+$N_H$2), $^{13}$C NMR ($CDCl_3$), 88.95, 132.87, 138.90, 194.33. This compound has the following structure:

EXAMPLE 3

4-Amino-17β-(cyclopropyloxy)androsta-4,6-dien-3-one

To a vigorously stirred mixture of the epoxide obtained as described in the first paragraph of Example 1 (2.4 g, 5.92 mM), in DMSO (50 ml), heated to 60° C., was added sodium azide (6.2 g, 95.5 mM) and then concentrated sulfuric acid (0.42 ml). The temperature was raised to 100° C. After 60

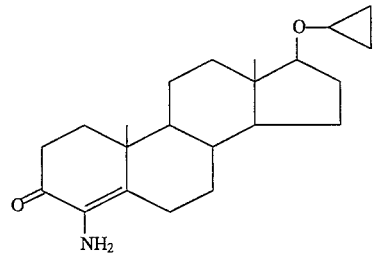

minutes at this temperature, the reaction was cooled to room temperature and poured into cold water (500 ml). The resulting precipitate was filtered off, washed with water, dried and purified by flash chromatography ($SiO_2$, toluene—5 to 20% ethyl acetate) to give 4-amino-17β-(cyclopropyloxy)androsta-4,6-dien-3-one (1.7 g, 84.0%). IR 3454, 3358, 1670, 1640, 1592 $cm^{-2}$; MS (CI) m/z 342 (70%, $M^+$+1), 284 (100%, $M^+$+1 —$C_3H_6O$); $^1$H NMR ($CDCl_3$) 0.38–0.64 (4H, m, 2×cyclopropyl $CH_2$'s), 0.84 (3H, s, $C_{18}$-Me), 1.06 (3H, s, $C_{19}$-Me), 3.0–3.9 (br s, $NH_2$), 3.25–3.35 (m, OCH), 3.48 (t, $C_{17}\alpha$-H), 5.95 (1H, dd), 6.30 (1H, dd); $^{13}$C NMR 88.66, 121.90, 132.15, 132.75, 135.69, 194.37. This compound has the following formula:

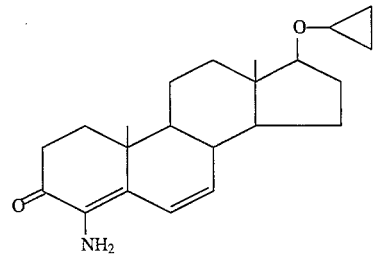

EXAMPLE 4

4-Amino-17β-(cyclopropyloxy)androst-4-en-3-one

17β-cyclopropyloxy-androst-4-en-3-one (9.70 g, 29.5 mM), potassium tert-butoxide (7.0 g, 62.4 mM), and isopropyl nitrate (2.99 ml) are reacted by the method of Example 1 to yield 17β-cyclopropyloxy-4-nitroandrost-4 -en-3-one, m.p. 137°–38° C. (methanol) IR ($CHCl_3$) , 1695, 1622(m) , 1535, 1373 $cm^{-1}$ MS(CI) 374(100%, M+10, 316(20%, M+1-c-$C_3H_5$-O)  $^1$H-NMR ($CDCl_3$) 0.38–0.61(4H, m), 0.80(3H, s, $C_{18}$-Me), 1.29(s, $C_{19}$-Me), 3.25–3.33(1H, m, cyclopropyl-CHO), 3.44(1H, t, $C_{17}$-H) .

The compound has the following structure:

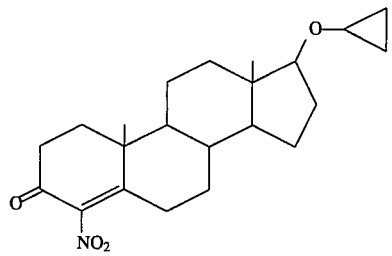

The starting material for the above nitration may be prepared as follows:

A solution of 17β-cyclopropyloxy-androst-5-en-3β-ol (19.36 g, 58.9 mM) in acetone (1.9 L) previously cooled to −3° C. is treated with Jones reagent (20 ml). The excess reagent is decomposed with methanol. The solids are removed by filtration. The filtrate is concentrated to a green oil which is purified by flash chromatography on silica gel to give 17β-cyclopropyloxy-androst-4-en-3-one (11.0 g, 57%).

The starting material (17β-cyclopropyloxy-androst-5-en-3β-ol) for the above oxidation may be prepared as described in U.S. Pat. No. 4,966,897 to Angelastro and Blohm.

The reduction of the 4-nitro compound may be done chemically in the following manner:

A solution of 17β-cyclopropyloxy-4-nitroandrost-4-en-3-one (1.0 g, 2.71 mM), either prepared above or by other known techniques, in acetic acid (10 ml) is treated with zinc dust (1.0 g). The combination (mixture) is vigorously stirred for 1.5 hours at room temperature. The zinc salts are removed by filtration and washed with ethyl acetate. The combined filtrate and wash are combined and concentrated to a yellow solid which is then redissolved in ethyl acetate and extracted three times with 1M hydrochloric acid (150 ml), The combined acid extracts are neutralized with sodium hydroxide (pH 14) and extracted with ether. The combined organic layers are then dried over sodium sulfate and concentrated to give 4-amino-17-cyclopropyloxyandrost-4-en-3-one (0.59 g), m.p. 100°–102° C. (aqueous methanol).

IR 3354, 1662, 1620, 1581 cm$^{-1}$ MS(CI) 344(100%, M+1) $^1$H-NMR 0.37–0.61(4H, m), 0.79(3H, s, $C_{18}$-Me), 1.16(s, $C_{19}$-Me), 3.25–3.33(m, cyclopropyl-CHO), 3.44(t, $C_{17}$-H).

The compound has the following structure:

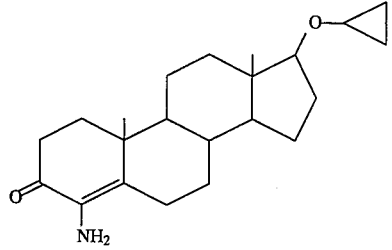

Alternatively, the reduction of the 4-nitro compound may be done catalytically in the following manner:

A solution of 17β-cyclopropyloxy-4-nitroandrost-4-en-3-one (4.36 g, 11.6 mM) in absolute ethanol (125 mL) was treated with Lindlar's catalyst and then quinoline (80 μL). The mixture was stirred under hydrogen atmosphere at 1 atm. pressure for about 117 hours. The reaction mixture was filtered through celite topped with charcoal and the solids washed with absolute ethanol. The combined filtrate and wash was concentrated to a brown liquid (3.7 g) and dissolved in methylene choride, placed atop a column of silica gel prepared with hexane:ethyl acetate (20:80) and purified by flash chromatagraphy taking 200 mL fractions and eluting in hexane:ethyl acetate (20:80).

The product containing fractions were combined and concentrated to yield a light yellow glass which crystallized on standing (2.3 g). The crystals were dissolved in methanol and filtered through cotton. Water was added dropwise until crystallization began, afterwhich the crystals were placed in a refrigerator overnight (12–18 hours). The crystals were collected by filtration and washed in cold aqueous methanol and again in water, then dried in vacuo to give 4-amino-17β-(cyclopropyloxy)-androst- 4-en-3-one as a light yellow solid (1.97 g). IR(KBr) ν3458, 3372, 1674, 1622 (m), 1585 cm$^{-1}$. Anal. calc'd for $C_{22}H_{33}NO_2$: C:76.92; H:9.68; N:4.08. Found: C:76.86; H:10.04; N:4.08. $^1$H-NMR (CDCl$_3$) δ 0.38–0.61 (4H, m, 2×CH$_2$), 0.79 (3H, s, $C_{18}$-Me), 1.15(s, $C_{19}$-Me), 3.27+3.44+ca.3.4 (4H, cycloproxy-H, $C_{17}$-H, NH$_2$, m+t, vbr.). $^{13}$C-NMR (CDCl3)δ 88.96, 132.92, 138.74, 194.30. UV(EtOH) λ 294(ε7570, lg.ε3.879) MS/CI 344(100%, M+1), 286(30%, M+1-C$_3$H$_5$OH)

EXAMPLE 5

4-Amino-17β-(cyclopropyloxy)androst-4-en-3-one hydrochloride

Dissolve 4-Amino-17β-(cyclopropyloxy)androst-4-en-3-one into ethyl acetate (20 mL) and treat with 4M hydrochloric acid in dioxane (about 2 mL). Remove the solvent on a rotary evaporator. Titrate the resulting solid with ethyl acetate to give a gelatinous material and heat in a steam bath until a solid separates. Cool the mixture to room temperature and dilute with an approximately equal portion of hexane. Filter the solid and wash in ethyl acetate:hexane (1:1) and dry to obtain the title compound. IR(KBr) ν 2675, 1662, 1641 cm$^{-1}$. MS(CI) 344 (100%, M+1), 286(30%, M+1, cyclopropyl-OH) $^1$H-NMR(CDCl$_3$) 0.38–0.61 (4H, m, 2×CH$_2$), 0.79(3H, s, $C_{18}$-Me), 1.25 (s, $C_{19}$-Me), 3.24 (1H, m, cyclopropyl-H), 3.42(1H, t, $C_{17}$), 9.74(2H, v.br., NH.HCl). Anal. calc'd for $C_{22}H_{34}ClNO_2$: C: 69.54, H: 9.02, N:3.69; Found: C:69.06, H: 8.89, N:3.94.

EXAMPLE 6

17β-cyclopropylamino-4-aminopregn-4-en-3-one

A solution of 17β-cyclopropylamino-4-en-3-one (4.61 g, 14.07 mmol) and potassium tert-butoxide (4.74 g, 42.22 mmol, 3 molar equivalents) in tert-butanol (60 mL) was heated at reflux for 1 hour. Isopropyl nitrate (1.43 mL, 14.07 mmol, 1 molar equivalent) was added all at once as the solution was refluxing. The reaction was slowly cooled to room temperature, after which glacial acetic acid (20 mL) and dichloromethane (20 mL) was added to the reaction mixture. The reaction was allowed to stand at room temperature overnight. The reaction mixture was filtered and the filter cake washed with dichloromethane until white. The filtrate was diluted with additional dichloromethane (200 mL) and subsequently washed with an aqueous sodium chloride solution at one-half the saturated concentration (200 mL) followed by a washing of a solution consisting of equal parts aqueous ½ saturated sodium chloride and aqueous saturated sodium bicarbonate (200 mL). The organic layer was dried over magnesium sulfate and concentrated in vacuo and purified by chromatagraphy on silica gel (19:1, dichloromethane:methanol) to give 17β-cyclopropylamino-4-nitroandrost-4-en-3-one as a solid yellow foam. $^1$H-NMR (300 MHz, CDCl$_3$) δ 0.75(s, 3H, $C_{18}$-Me); 1.30 (s, 3H, $C_{18}$-Me ) ppm. $^{13}$C-NMR (75 MHz, CDCl$_3$) δ 6.46, 7.20, 11.70, 17.64, 20.79, 23.54, 27.07, 29.62, 29.68, 30.84, 33.03, 34.06, 35.11, 37.54, 39.16, 42.40, 52.37, 53.75, 68.84, 146.66, 160.73, 187.47 ppm. IR (KBr) 3435, 2944, 2870, 1695, 1533, 1371, 1013, 766 cm$^{-1}$. MS (EI) 372 (M$^+$).

The compound has the following structure:

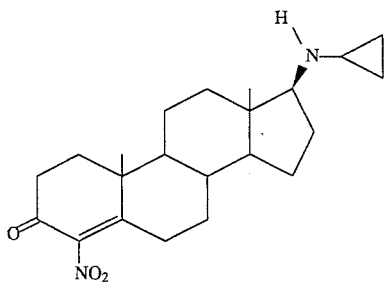

17β-cyclopropylamino-4-nitroandrost-4-en-3-one prepared by the above procedure (670 mg, 1.80 mmol) was dissolved in absolute ethanol (11 mL) and treated with Lindlar catalyst (5.95 Pd+5.4% Pb) (268 mg) followed by quinoline (3 μL). The solution was stirred vigorously under H2 atmosphere at atmospheric pressure (about 760 mm/mg) for 18 hours. The reaction mixture was filtered and washed with ethanol (100 mL) and dichloromethane (100 mL). The solvents were removed in vacuo and the product purified by chromatagraphy on silica gel (47:3, CH$_2$Cl$_2$:CH$_2$OH) to give a yellow oil which crystallized to a yellowish solid. m.p. 149°–150° C. (Et$_2$O). IR(KBr): 3474, 3366, 2945, 1616, 1577, 1441, 1369, 1170, 1011 cm$^{-1}$ MS(CI/CH$_4$) [M$^+$+H] 343 $^1$H-NMR (33 MHz, CDCl$_3$) δ 0.73(s, 3H, C$_{18}$-Me), 1.15(s, 3H, C$_{19}$-Me), 2.66 (t, J=9.3 Hz, 1H, C$_{17}$-H) $^{13}$C-NMR (75 MHz, CDCl$_3$) δ 6.464, 7.185, 11.289, 20.803, 23.682, 24.757, 29.683, 29.753, 30.914, 32.860, 34.899, 35.307, 37.904, 42.453, 52.910, 54.549, 69.014, 132.938, 138.860, 194.343.

The compound has the following structure:

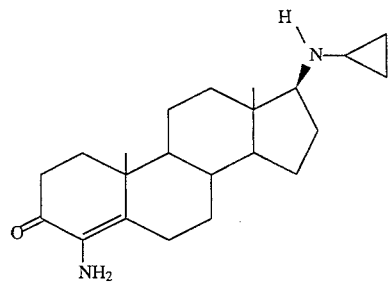

What is claimed is:

1. A compound and the pharmaceutically acceptable salts of the formula:

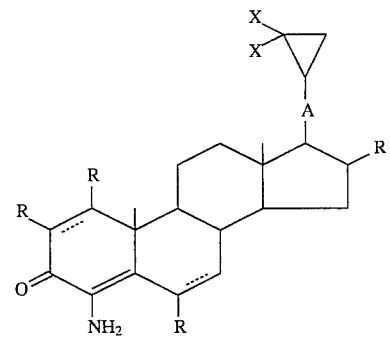

wherein A is O or NH and each R is independently selected from the group consisting of hydrogen and C$_1$-C$_4$ lower alkyl; each X is independently selected from the group consisting of hydrogen, halogen, and methyl; and the dotted lines indicate the optional presence of a double bond.

2. A compound according to claim 1 which is 4-amino-17β -(cyclopropyloxy)androst-4-en-3-one.

3. A compound according to claim 1 which is 4-amino-17β-(cyclopropyloxy)androsta-4,6-diene-3-one.

4. A compound according to claim 1 which is 4-amino-17β -(cyclopropylamino)androst-4-en-3-one.

5. A pharmaceutical composition having C$_{17\text{-}20}$ lyase and 5α-reductase inhibiting activity, in a dosage unit form, comprising a pharmaceutical carrier and a compound and the pharmaceutically acceptable salts of the formula

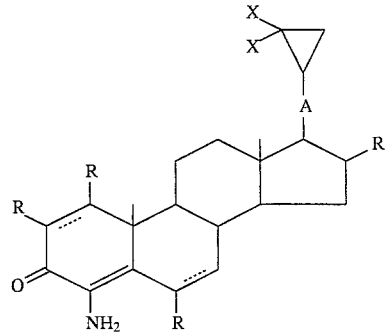

wherein A is O or NH and each R is independently selected from the group consisting of hydrogen and C$_1$-C$_4$ lower alkyl; each X is independently selected from the group consisting of hydrogen, halogen, and methyl; and the dotted lines indicate the optional presence of a double bond.

6. A pharmaceutical composition according to claim 5 wherein the compound is 4-amino-17β -(cyclopropyloxy)androst-4-en-3-one.

7. A pharmaceutical composition according to claim 5 wherein the compound is 4-amino-17β -(cyclopropyloxy)androsta-4,6-diene-3-one.

8. A pharmaceutical composition according to claim 5 wherein the compound is 4-amino-17β -(cyclopropylamino)androst-4-en-3-one.

9. A method of inhibiting C$_{17,20}$ lyase enzyme which comprises administering to a patient in need thereof an effective inhibitory amount of a compound and the pharmaceutically acceptable salts of the formula:

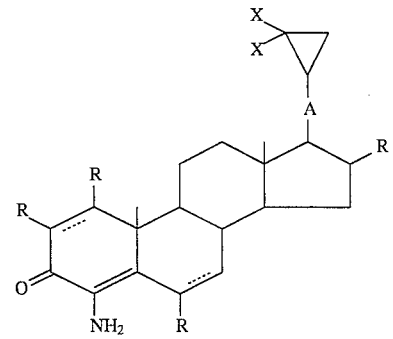

wherein A is O or NH and each R is independently selected from the group consisting of hydrogen and C$_1$-C$_4$ lower alkyl; each X is independently selected from the group consisting of hydrogen, halogen, and methyl; and the dotted lines indicate the optional presence of a double bond.

10. A method according to claim 9 wherein the compound is 4-amino-17β-(cyclopropoxy)androst-4-en-3-one.

11. A method according to claim 9 wherein the compound is 4-amino-17β-(cyclopropoxy)androsta-4,6-dien-3-one.

12. A method according to claim 9 wherein the compound is 4-amino-17β-(cyclopropylamino)androst-4-en-3-one

13. A method of inhibiting 5α-reductase enzyme which comprises administering to a patient in need thereof an effective inhibitory amount of a compound and the pharmaceutically acceptable salts of the formula:

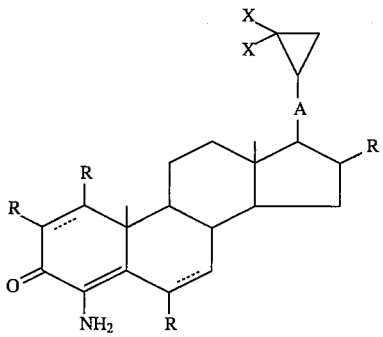

wherein A is O or NH and each R is independently selected from the group consisting of hydrogen and $C_1$-$C_4$ lower alkyl; each X is independently selected from the group consisting of hydrogen, halogen, and methyl; and the dotted lines indicate the optional presence of a double bond.

14. A method according to claim 13 wherein the compound is 4-amino-17β-(cyclopropoxy)androst-4-en-3-one.

15. A method according to claim 13 wherein the compound is 4-amino-17β-(cyclopropoxy)androsta-4,6-dien-3-one.

16. A method according to claim 13 wherein the compound is 4-amino-17β-(cyclopropylamino)androst-4-en-3-one.

17. A method for treating androgen-dependent disorders which comprises administering to a patient in need thereoff an effective inhibitory amount of a compound and the pharmaceutically acceptable salts of the formula:

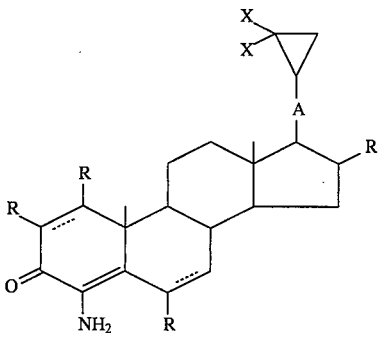

wherein A is O or NH and each R is independently selected from the group consisting of hydrogen and $C_{1-4}$ lower alkyl; each X is independently selected from the group consisting of hydrogen, halogen, and methyl; and the dotted lines indicate the optional presence of a double bond.

18. A method according to claim 17 wherein the compound is 4-amino-17β-(cyclopropoxy)androst-4-en-3-one.

19. A method according to claim 17 wherein the compound is 4-amino-17β-(cyclopropoxy)androsta-4,6-diene-3-one.

20. A method according to claim 17 wherein the compound is 4-amino-17β-(cyclopropylamino)androst-4-en-3-one.

21. A method for treating estrogen-induced or estrogen-stimulated disorders, which comprises administering to a patient in need thereof an effective inhibitory amount of a compound and the pharmaceutically acceptable salts of the formula:

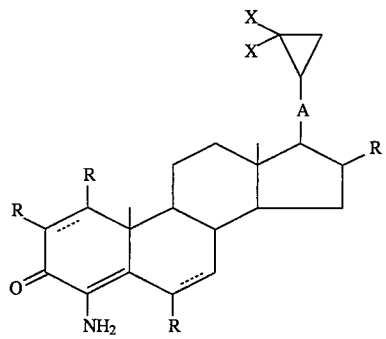

wherein A is O or NH and each R is independently selected from the group consisting of hydrogen and $C_1$-$C_4$ lower alkyl; each X is independently selected from the group consisting of hydrogen, halogen, and methyl; and the dotted lines indicate the optional presence of a double bond.

22. A method according to claim 21 wherein the compound is 4-amino-17β-(cyclopropoxy)androst-4-en-3-one.

23. A method according to claim 21 wherein the compound is 4-amino-17β-(cyclopropoxy)androst-4,6-dien-3-one.

24. A method according to claim 21 wherein the compound is 4-amino-17β-(cyclopropylamino)androst-4-en-3-one.

25. A method of treating a DHT-mediated disease which comprises administering to a patient in need thereof an effective inhibitory amount of a compound and the pharmaceutically acceptable salts of the formula:

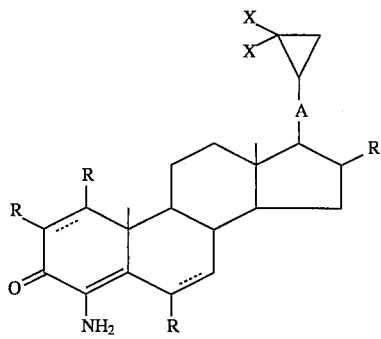

wherein A is O or NH and each R is independently selected from the group consisting of hydrogen and $C_1$-$C_4$ lower alkyl; each X is independently selected from the group consisting of hydrogen, halogen, and methyl; and the dotted lines indicate the optional presence of a double bond.

26. A method according to claim 25 wherein the compound is 4-amino-17β-(cyclopropoxy)androst-4-en-3-one.

27. A method according to claim 25 wherein the compound is 4-amino-17β-(cyclopropoxy)androsta-4,6-dien-3-one.

28. A method according to claim 25 wherein the compound is 4-amino-17β-(cyclopropylamino)androst-4-en-3-one.

29. A method of treating benign prostatic hyperplasia which comprises administering to a patient in need thereof an effective inhibitory amount of a compound and the pharmaceutically acceptable salts of the formula:

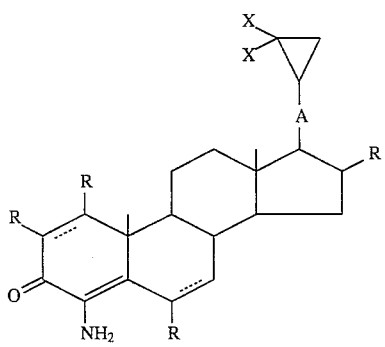

wherein A is O or NH and each R is independently selected from the group consisting of hydrogen and $C_1$-$C_4$ lower alkyl; each X is independently selected from the group consisting of hydrogen, halogen, and methyl; and the dotted lines indicate the optional presence of a double bond.

30. A method according to claim 29 wherein the compound is 4-amino-17β-(cyclopropoxy)androst-4-en-3-one.

31. A method according to claim 29 wherein the compound is 4-amino-17β-(cyclopropoxy)androsta-4,6-dien-3-one.

32. A method according to claim 29 wherein the compound is 4-amino-17β-(cyclopropylamino)androst-4-en-3-one.

33. A method of treating breast cancer which comprises administering to a patient in need thereof an effective inhibitory amount of a compound and the pharmaceutically acceptable salts of the formula:

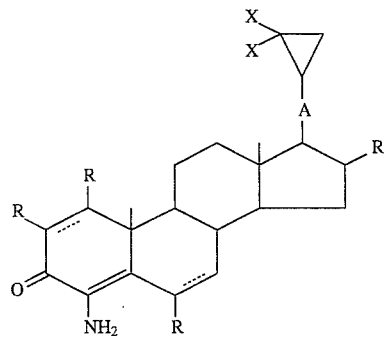

wherein A is O or NH and each R is independently selected from the group consisting of hydrogen and $C_1$-$C_4$ lower alkyl; each X is independently selected from the group consisting of hydrogen, halogen, and methyl; and the dotted lines indicate the optional presence of a double bond.

34. A method according to claim 33 wherein the compound is 4-amino-17β-(cyclopropoxy)androst-4-en-3-one.

35. A method according to claim 33 wherein the compound is 4-amino-17β-(cyclopropylamino)androst-4-en-3-one.

36. A method of treating prostate cancer which comprises administering to a patient in need thereof an effective inhibitory amount of a compound and the pharmaceutically acceptable salts of the formula:

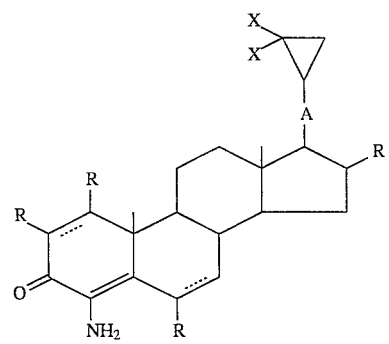

wherein A is O or NH and each R is independently selected from the group consisting of hydrogen and $C_1$-$C_4$ lower alkyl; each X is independently selected from the group consisting of hydrogen, halogen, and methyl; and the dotted lines indicate the optional presence of a double bond.

37. A method according to claim 36 wherein the compound is 4-amino-17β-(cyclopropoxy)androst-4-en-3-one.

38. A method according to claim 36 wherein the compound is 4-amino-17β-(cyclopropylamino)androst-4-en-3-one

* * * * *